United States Patent
Ohta et al.

(10) Patent No.: US 6,336,910 B1
(45) Date of Patent: Jan. 8, 2002

(54) EXTRACORPOREAL CIRCULATION APPARATUS FOR SELECTIVE COOLING METHOD

(75) Inventors: Tomio Ohta, Osaka; Takuichi Kobayashi, Shiga-ken, both of (JP)

(73) Assignee: Tomio Ohta, Osaka-fu (JP)

( * ) Notice: Subject to any disclaimer, the term of this patent is extended or adjusted under 35 U.S.C. 154(b) by 0 days.

(21) Appl. No.: 09/187,986

(22) Filed: Nov. 9, 1998

(51) Int. Cl.$^7$ .................. A61M 37/00; A61M 1/36; A61M 1/14; C02F 1/00; B01D 61/00

(52) U.S. Cl. .................. 604/6.13; 604/4.01; 604/5.01; 604/6.09; 604/6.11; 604/6.15; 422/44; 210/742; 210/767; 128/DIG. 3

(58) Field of Search .................. 604/4–6, 4.01, 604/5.01, 6.01–6.07, 6.11, 6.13, 6.15–6.16; 422/44–46; 210/739, 742, 767, 85, 88; 128/905, DIG. 3, 203.26–203.27

(56) References Cited

U.S. PATENT DOCUMENTS

| | | | |
|---|---|---|---|
| 5,069,662 A | * 12/1991 | Bodden | 604/4 |
| 5,178,603 A | * 1/1993 | Prince | 604/4.01 |
| 5,344,392 A | * 9/1994 | Senninger et al. | 604/4.01 |
| 5,423,738 A | * 6/1995 | Robinson et al. | 604/4.01 |
| 5,674,190 A | * 10/1997 | Kelly | |
| 5,783,093 A | * 7/1998 | Holme | 210/767 |
| 5,817,045 A | * 10/1998 | Sever, Jr. | |
| 5,899,873 A | * 5/1999 | Jones et al. | |
| 5,906,588 A | * 5/1999 | Safar et al. | |

OTHER PUBLICATIONS

"Profound Hypotension with Differential Cooling of the Brain in Dogs", J. Neurosurg 24:993–1001, 1966.

"Selective Cooling of Brain Using Profound Hemodilution in Dogs", Neurosurgery vol. 31, No. 6, Dec. 1992 (pp. 1049–1055).

"Selective Hypothermic Perfusion of Canine Brain", Neurosurgery vol. 38, No. 6, Jun. 1996 (pp. 1211–1215), OHTA et al.

* cited by examiner

Primary Examiner—Angela D. Sykes
Assistant Examiner—Patricia Bianco
(74) Attorney, Agent, or Firm—Wenderoth, Lind & Ponack, L.L.P.

(57) ABSTRACT

An extracorporeal circulation apparatus capable of maintaining hypothermia for a prolonged period when used in the selective cooling method.

The extracorporeal circulation apparatus used in the selective cooling method includes (1) a diluent supply unit for cooling a diluent and metering the diluent into a blood vessel; (2) a blood concentration unit for metering a diluted blood out from a blood vessel and concentrating the diluted blood thus drawn out by filtering the diluted blood; and (3) a blood supply unit for heating the concentrated blood and metering the concentrated blood into a blood vessel, wherein a flow rate of the injected diluent flow rate, Vd and a flow rate of a filtrate, Vb are so controlled that a relationship $0.1 \, Vd \leq Vb \leq Vd$ is maintained.

31 Claims, 2 Drawing Sheets

EXTRACORPOREAL CIRCULATION APPARATUS FOR SELECTIVE COOLING METHOD

BACKGROUND OF THE INVENTION

1. Field of the Invention

The present invention relates to a novel extracorporeal circulation apparatus used when conducting a selective (or exclusive) cooling method employed in various medical treatments in mammals, especially in humans.

2. Description of the Related Art

Since Woodhall introduced in 1960 a systemic profound hypothermia under a cardiac arrest for the purpose of protecting a brain against a hemorrhage or an ischemia upon a craniotomy, the systemic profound hypothermia has been employed in many types of operations. However, a pump-oxygenator employed in this method makes the procedure complicated and the blood perfusion to various organs insufficient and the method requires a large amount of heparin as an anticoagulant, resulting in problems such as a secondary cerebral hemorrhage.

One of the inventors had made an effort to overcome the problems mentioned above and had developed a method for cooling a brain selectively (which is substantially similar in its meanings to the abovementioned "selective cooling method") while using a pump-oxygenator, and applied the method to a craniotomy (J. Neurosurg; Vol 24, pages 994 to 1001, 1966)). This selective cooling method did provide a cerebral hypotension safely but still involved problems with regard to the intra- and post-operative hemorrhages due to the use of a large amount of heparin still associated therewith.

In order to overcome these problems, one of the inventors discovered a method for injecting a cooled lactated Ringer's solution into a cerebral artery to cool a brain exclusively and to dilute a blood simultaneously with the cooling of the blood, resulting in a substantially reduced heparin level, thereby reducing the risk of the hemorrhage (see Neurosurgery Vol 31, pages 1049 to 1055, 1992)). This method allows a reversible extreme hypotension to be established without undergoing an oxygen deficit and enables an extreme reduction in the amount of heparin to be used as a result of introduction of the cooled diluent, thereby allowing such an amount to be close to that used in an ordinary angiography. In addition, the introduction of the diluted blood into a lesion leads to various safety-improving effects such as reduction in blood loss.

SUMMARY OF THE INVENTION

As described above, by injecting the cooled lactated Ringer's solution, a temperature of a brain is reduced. However, a volume of the lactated Ringer's solution to be injected is generally large and therefore, the injection of the lactated Ringer's solution allows the blood to be diluted excessively, thereby increasing a volume of circulating blood, which leads to humoral plethora, resulting in difficulty in maintaining the hypothermia for a sufficient period, due to which a satisfactory hypotension in the brain cannot be ensured. In addition, a large volume of the cooled diluted blood distributed throughout the entire body may cause problems such as reductions in body temperature and blood activity, a necessity for adjusting the blood electrolyte balance as well as an overhydration which is difficult to control only by a diuretic.

Accordingly, we have made an effort to solve the problems mentioned above, and finally discovered a novel extracorporeal circulation apparatus.

In a first aspect, the present invention provides an extracorporeal circulation apparatus used to perform the selective cooling method conveniently, and said apparatus comprises a diluent supply unit for cooling a diluent to a temperature below a body temperature and metering the diluent into a blood vessel, a blood concentration unit for metering diluted blood out from a blood vessel and concentrating the diluted blood thus drawn out to obtain a hematocrit value which is preferably at least 80% of the hematocrit value of the blood before dilution, and a blood supply unit for heating the concentrated blood to a temperature close to the body temperature and metering it into a blood vessel.

Accordingly, in a second aspect, the present invention resides in a method for applying the selective cooling method to a predetermined part (or a subject) of a mammal, especially of a human body, comprising, injecting a cooled diluent into a body at a site having an artery which is in direct or indirect communication with the part to be cooled, drawing a blood diluted with the diluent out from the body at a site having a vein which is in direct or indirect communication with said part, concentrating the diluted blood to recover blood in a state similar to that before the dilution, preferably blood substantially equivalent to the blood before the dilution, and, warming the recovered blood and then returning the warmed blood to the body at a venous site which is in direct or indirect communication with said vein and is closer to the heart.

Moreover, there is provided a method for treating a predetermined part of a mammal, especially of a human body, by means of applying the selective cooling method according to the second aspect to said part using the extracorporeal circulation apparatus according to the first aspect. Thus, in a third aspect, there is also provided a method for a treatment wherein the extracorporeal circulation method according to the second aspect is performed using the extracorporeal circulation device according to the first aspect, and the method includes a method for an operation and a method for controling a condition.

In the present invention, the term "selective cooling method" means a method used in a medical field, especially in the field of a cerebral surgery, and means a method for selecting as a target part a part of a body, for example, an organ such as a brain, and then cooling said part locally. The selective cooling method is a locally cooling method used, for example, when a hemorrhage is predicted such as in a case of performing a surgical operation in a certain local region in a body (for example, the head), or when an operation is performed during a period in which a vital activity is reduced locally and transiently.

Figure 1:
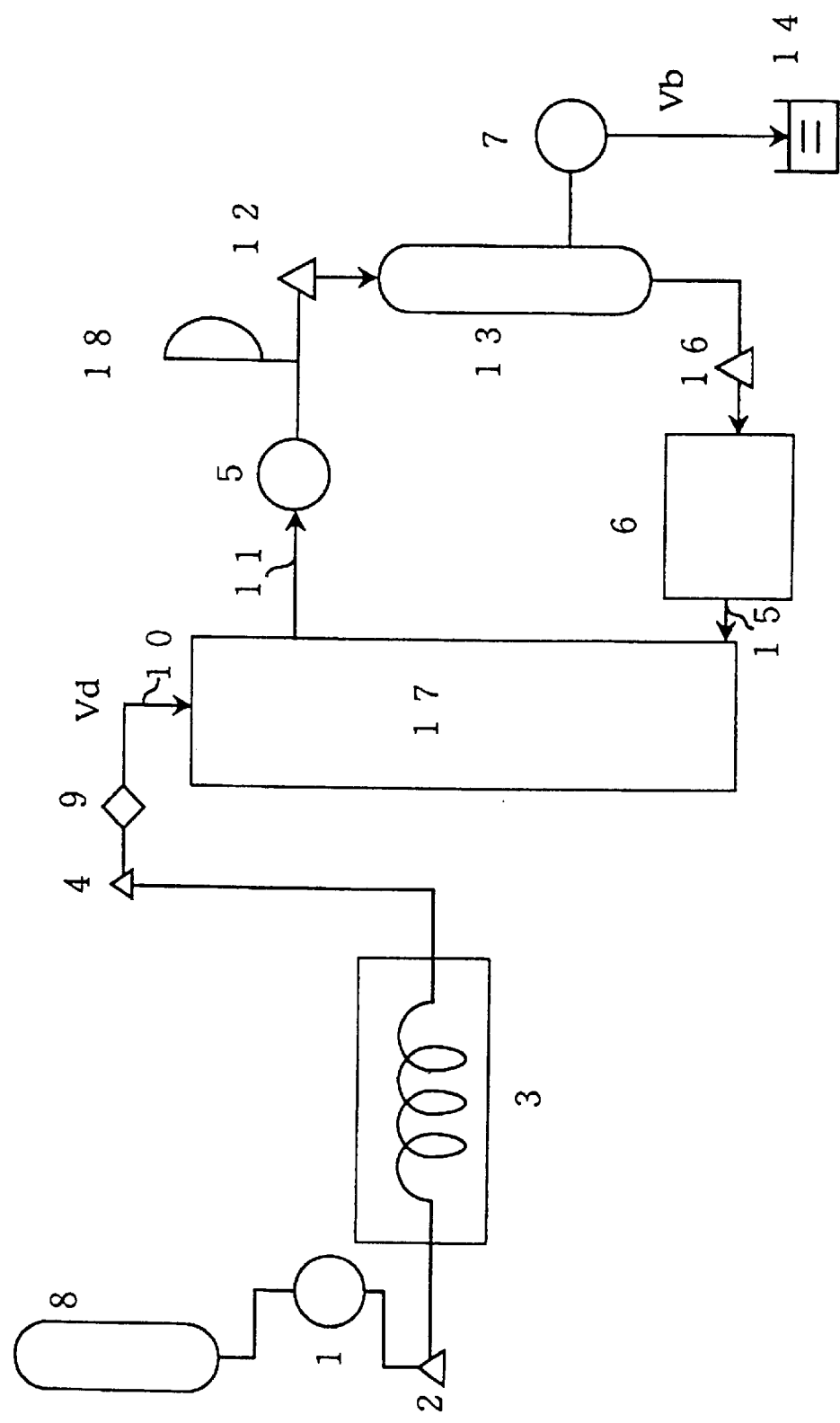
FIG. 1 shows a schematic view of an apparatus according to the present invention.

In the figures, the following numbers are referred to for designating the corresponding elements. 1: Fluid supply pump, 2: Flow meter, 3: Heat exchanger, 4: Thermometer, 5: Drawing-out (fluid supply) pump, 6: Heat exchanger, 7: Filtrate pump, 8: Diluent container, 9: Drip chamber, 10, 11: Catheter, 12: Drip chamber, 13: Concentration element, 14: Filtrate receiver, 15: Catheter, 16: Drip chamber, 17: Body, 18: Heparin supplier, 19: Injection/dehydration controlling mechanism.

DETAILED DESCRIPTION OF THE INVENTION

The present invention is based on the understanding that, by injecting a cooled diluent into a body at a site having an artery which is in a direct or indirect communication with a part to be cooled, drawing blood diluted with the diluent out of the body at a site having a vein which is in a direct or indirect communication with said part, thereafter concentrating the diluted blood to recover blood in a state similar to that before the dilution, preferably blood substantially equivalent to the blood before the dilution, and warming the recovered blood (for example to a temperature close to a body temperature) and then returning the warmed blood to the body at a venous site which is in a direct or indirect communication with said vein and which is closer to the heart (thus a proximal site or a heart site), said part can safely be cooled without causing a significant change, preferably without a substantial increase, in the humoral volume retained in the body.

For example, when the selective cooling method is applied to a brain, the diluent is injected into a body at a cervical part via a vertebral artery, diluted blood is drawn out from the body via a jugular vein, and concentrated blood is returned into the body via a femoral vein. When applying to a liver, the diluent is injected via a hepatic artery and diluted blood is drawn out via a suitable vein, for example, a hepatic vein. Concentrated blood is returned to the body through a venous site close to the heart (i.e. proximal site). Generally, the diluent is injected into an artery which belongs (or leads) to a part to which the selective cooling method is applied, and a vein through which the diluted blood is drawn out and a vein through which the concentrated blood is returned are not limited particularly.

By using the apparatus according to the present invention, the problems such as a complicated procedure associated with a use of a pump-oxygenator under a cardiac arrest as well as various risks such as a risk of hemorrhage can be overcome and a safe hypotension is ensured while avoiding an extreme overhydration.

The diluent employed in the apparatus according to the present invention may be any diluent which can be cooled by a suitable method and which can be used for diluting blood after being supplied to a body through a blood vessel and for cooling internally a part to be treated. Generally, a diluent is one which at least does not affect an intended treatment adversely, and preferably one which contributes to such a treatment. Concretely, it is especially preferred to use as a diluent an aqueous solution containing nutrients and electrolytes, such as a Ringer's solution, a lactated Ringer's solution, a Ringer's solution containing a low molecular weight dextrin (for example contained at 5%), which are only non-limiting examples.

In the apparatus according to the present invention, the cooling of the diluent and the warming of the concentrated blood are performed preferably by means of heat exchange, particularly by means of indirect heat exchange. A device used for the purpose mentioned above is not particularly limited. One heat exchange method for making the temperature of a diluent or a concentrated blood at predetermined temperatures is immersing a tube through which each fluid is transported in a thermostat tank which has been set up at a predetermined cooling or heating temperature, and such a heat exchange method is preferable.

A temperature to which the diluent is cooled depends on the type of the treatment, a time period required for the treatment as well as conditions of a patient, and thus is not particularly limited. Generally, the diluent is cooled to a temperature within the range generally from a temperature below a body temperature to 3° C., preferably from 25° C. to 3° C., more preferably from 18° C. to 3° C. Since the concentrated blood is returned to a body preferably at a temperature close to the body temperature for the purpose of maintaining the functions of the internal organs, the cooled blood, after being concentrated, is warmed by means of heat exchange preferably to a temperature close to the body temperature, i.e. generally 32° C. to 38° C., for example at about 37° C. or 38° C., prior to returning in the body.

In the apparatus according to the present invention, the concentration of the blood means the increase in or the recovery of the hematocrit value of the diluted blood drawn out from a body (thus the diluted blood has a hematocrit value lower than that of an initial blood (i.e. blood before the dilution)), and can concretely be performed by means of a filtration or dialysis treatment. Such a treatment may be performed by using an ordinary hemofilter or dialyzer which is generally used in, for example, an artificial kidney apparatus. In the apparatus according to the present invention, the concentrated blood has a hematocrit value which is at least about 80%, preferably at least about 90%, more preferably at least about 95% of the hematocrit value of the blood before the dilution, and, most preferably, substantially equivalent to that before the dilution.

Actually in an embodiment using the apparatus according to the present invention, a hematocrit value of a normal human, which is about 40 to 50%, is reduced, as a result of the dilution, to about 5 to 20%, for example to about 7%, and is increased to about 30 to 50% after concentration. Accordingly, a hematocrit recovery rate in such a case (a hematocrit value after the concentration/a hematocrit value before the dilution) is about 0.8 to 1.00.

Concrete Embodiments of the Invention

The apparatus according to the present invention is further explained in detail below referring to attached drawings.

FIG. 1 shows a schematic view (a flow sheet) of an extracorporeal circulation apparatus according to the present invention.

The extracorporeal circulation apparatus shown in FIG. 1 comprises a diluent supply unit comprising a diluent container (8), a fluid supply pump (1) by which a diluent is injected from the container (8) into a body (17), a supply flow meter (2), a heat exchanger (3) for cooling the diluent, a thermometer (4) and a drip holder (9), a blood concentration unit comprising a drawing-out/fluid supply pump (5) which draws a diluted blood from the body (17) and finally returns a recovered concentrated blood into the body (17), a heparin supplier (18), a drip chamber (12), a blood concentration device (13), a filtrate pump (7) and a filtrate receiver (14), and a blood supply unit comprising a drip chamber (16) and a heat exchanger (6) which heats the concentrated blood. These units and their elements are connected appropriately with each other via suitable tubes (for example, silicone tubes, polyvinyl chloride tubes and the like), and necessary communications between each unit and a body (17) are established via catheters (10, 11 and 15).

In the diluent supply unit, the fluid supply pump (1) and the heat exchanger (3) for cooling should be provided. The fluid supply pump (1) is capable of injecting the diluent quantitatively into the body (17) usually at a flow rate of 100 to 600 ml/min, preferably 200 to 500 ml/min, and more preferably 250 to 400 ml. A practical flow rate of the pump may vary as necessary, within the range specified above, depending on the purpose of the treatment. A pump capable of injecting the diluent quantitatively (thus capable of metering-in) may, for example, be a roller pump employed frequently for pumping blood. For the purpose of rapid cooling, a relatively higher flow rate is preferable, and a flow rate of 100 to 400 ml/min is employed more preferably.

Flow meter (2) serves to determine the flow rate of the diluent supplied, and may, for example, be an electromagnetic flow meter, and preferably has a controlling function capable of adjusting the flow rate at a predetermined rate when the flow rate is once deviated therefrom (for example a function to change the rotation speed of a pump motor, or to change the pressure loss of a conduit). When the (1) is capable of controlling quantity fluid supply pump, then flow meter (2) may be deleted. While no flow meter is provided in the conduit in the other unit in the apparatus shown in the drawings, a flow meter may be provided in any conduit through which a fluid should be pumped at a predetermined flow rate, thereby establishing a cooperation of the flow meter with the pump to ensure a flow at a predetermined rate (thus establishing metered drawing-out or injection).

The heat exchanger (3) for cooling may be any device which can cool the diluent to a predetermined temperature within the range usually from a temperature below a body temperature to 3° C., preferably from 25 to 3° C., more preferably from 18 to 3° C. This heat exchanger (3) keeps the temperature of the injected diluent at a predetermined temperatures by cooperating with a thermometer (4) which determines the temperature of the diluent. It is a matter of course that the thermometer (4) may be absent when the heat exchanger by itself can maintain the predetermined temperature of the diluent. This may be applied similarly to a heat exchanger (6) in a blood supply unit, and a thermometer is not shown in the blood supply unit in FIG. 1.

When using the apparatus according to the present invention, the diluent is pumped from the container (8) via the fluid supply pump (1) and the flow meter (2) to the heat exchanger (3) for cooling where it is cooled, and then injected via a blood vessel which is in communication with a part to which the local cooling method is applied, usually via an arterial catheter (10), into a body (17). In such case, a catheter is inserted into the blood vessel (artery) in communication with the site to which the selective cooling method is applied, but the location of the insertion may not necessarily be adjacent to the part to be cooled. A method, such as Seldinger's method, in which the diluent is injected via a catheter that is inserted percutaneously via a femoral artery to a brain may also be included. In such a case, a body temperature-lowering effect is associated, but is not problematic as long as the temperature does not become as low as 30° C. or lower. The container (8) may be a plastic container or a polyethylene bag containing the diluent, or may be a tank holding the diluent transferred from such containers.

In addition to the elements described above, a drip chamber (9) for bubble removal may also be provided in the diluent supply unit, thereby separating the air bubbles, if any, contained in the diluent. The same applies analogously to the blood concentration unit and the blood supply unit.

The apparatus according to the present invention has the blood concentration unit which meters the diluted blood out from a blood vessel, usually a vein, through which the diluted blood runs after having passed through the part to be cooled, and which concentrates the blood to obtain the hematocrit value which is preferably substantially the same as that of original blood, and this unit should have a drawing-out/fluid supply pump (5) which meters the diluted blood out from a body (17) and then pumps it, as well as an element (13) for concentrating the diluted blood which has been drawn out and then pumped thereto.

This pump (5) preferably draws the diluent blood quantitatively from the body via a catheter (11) at rate generally of 50 to 300 ml/min, preferably 100 to 300 ml/min, and more preferably 150 to 300 ml/min. A practical flow of the pump (5) may be selected as necessary from the range specified above, depending on the purpose of the treatment. The pump (5) may be similar to the diluent supply pump (1), and may cooperate with a flow meter (not shown) as described above.

When using the apparatus according to the present invention, the diluted blood is drawn out via a vein extending from the part to be cooled selectively using the catheter (11). The diluted blood runs through fluid supply pump (5) and is introduced into a blood inlet of the blood concentration element (13) which is preferably a disposable product.

In the apparatus according to the present invention, the concentration element (13) is preferably a filtration device as described above, and is controlled preferably based on the hematocrit values of the blood before dilution and after concentration. The hematocrit value is determined by subjecting concentrated blood to centrifugation and then calculating a volume ratio (%) of blood cells.

Alternatively, it is preferable to avoid an excessive overhydration in a patient by controlling the apparatus based on the determined values of a flow rate of the diluent supplied, a flow rate of the filtrate, a total volume of the diluent supplied, and a total volume of the filtrate, and it is usually sufficient to control the apparatus in this way.

The filtration device may have a pump (7) on the side of the filtrate, if necessary to increase the pressure difference between both sides of the filter material (thus giving a broader controllable range of the filtration pressure), thereby providing greater versatility of the flow rate of the filtrate. The concentration element (13) may of course effect filtration by means only of the pressure difference between the pressure of the diluted blood (delivery pressure) given by the pump (5) and the pressure of filtrate (atm o spheric pressure) (i.e. so-called spontaneous filtration). In the case of spontaneous filtration, the filtrate can be collected into filtrate receiver (14) without passing through a pump (7).

When the pump (1) is working a fluid, it is preferable that the flow rate of the filtrate from the filtration device (13) (Vb ml/min) is substantially lower than the flow rate of the diluent injected into the body (Vd ml/min), but is still kept at a certain rate or higher. This is based on the understanding that for the purpose of ensuring the effective cooling performance of the diluent, it is preferable to retain a certain volume of the diluent transiently at the part to be cooled. Accordingly, in a preferable embodiment of the apparatus according to the present invention, the certain rate of the flow rate of the filtrate is so controlled that a relationship 0.1 Vd≦Vb≦Vd (wherein Vd≠0) is maintained. A flow rate Vb less than 0.1 Vd (i.e. Vb<0.1 Vd) is not preferable since the humoral volume is increased transiently to an undesirably excessive volume. On the other hand, a flow rate Vb substantially greater than Vd is not preferable since the blood is concentrated excessively. Nevertheless, in the apparatus according to the present invention, th flow rate Vb higher than Vd is not completely excluded and may be acceptable as long as the treatment employing the apparatus according to the present invention is not affected adversely.

In the apparatus according to the present invention, the filtrate consists substantially of an aqueous solution containing as main components (solutes), low molecular weight substances (for example, an electrolyte and a saccharide such as glucose), and it is most preferable that the total volume of the filtrate generated during the use of the apparatus according to the present invention is equivalent to the total volume of the diluent supplied during this period. Accordingly, taking the preferable relationship 0.1

Vd≦Vb≦Vd described above into consideration, the pump (1) and the pump (5), as well as the pump (7), if any, may be operated for different periods, and the flow rate Vb may be a significant value as a result of the pump (5) being operated even if the pump (1) is not operated. The total volume of the filtrate and the total volume of the diluent supplied may not necessarily be substantially the same, and may be different from each other as long as the treatment is not adversely affected. Based on such understanding, it is generally acceptable to maintain only a relationship 1.0× the total volume of the filtrate ≦ the total volume of the diluent supplied ≦1.2× the total volume of the filtrate. Since it naturally takes a certain period to allow the diluent once supplied to pass through the part to be cooled and then to be drawn out, it is not necessary to initiate the operations of the pumps (5) and (7) simultaneously with the operation of the pump (1). When the diluent supplied may be excreted as urine in an actual treatment, a volume of the urine is included in the total filtrate volume in the present specification. Thus, the urine is regarded as filtrate when discussing the relationship described above. Nevertheless, a urine flow rate is not included in the filtrate flow rate Vb.

In the apparatus as embodied in the drawing, the fluid supply pump (5) has a function for drawing the diluted blood out from the body (17), a function for transporting the blood to the concentration element (13) thereby enabling concentration, and a function for then returning the concentrated blood thus obtained into the body (17). It is obvious to those skilled in the art that these functions may be effected by means of independent pumps, between any two of which a buffer (or a reservoir) is provided.

The blood concentration unit in the apparatus according to the present invention may be provided with a drip chamber (12) for the removal of bubbles as well as an anticoagulant supply unit (18), for example a heparin supplier, if necessary. An anticoagulant (such as heparin or FUSANE and the like) may be supplied at any location in the apparatus according to the invention. While in the embodiment shown in the drawing, the heparin supplier (18) is provided in the blood concentration unit as described above, the heparin supplied does not migrate substantially into the filtrate (thus remains in the concentrated blood) even if it passes through the blood concentration element (13).

The apparatus according to the present invention has the blood supply unit for heating a low-temperature blood which has been concentrated to a temperature close to a body temperature and then injecting it into a blood vessel (vein). Concretely, such a unit has a heat exchanger (6) for heating the blood to a temperature near 37° C. and then injecting it into the vein which is usually closer to the heart. Concretely, during the use of the apparatus according to the present invention, the concentrated blood passes through the heat exchanger (6) for heating via a conduit connected to a blood outlet of the blood concentration device (13), and then is injected into the vein via a catheter (15). In such a case, a drip chamber (16) for removing bubbles may be provided as illustrated in the drawing.

In a preferred embodiment of the present invention, an injection/dehydration (fluid removal) controlling mechanism capable of automatically controlling the flow rate of the diluent injected and the flow rate of the diluted blood drawn out as well as the flow rate of the filtrate flow rate is provided for the purpose of maintaining the humoral volume at a desired volume by balancing each flow rate. When urine is excreted, the flow rates may also be controlled including the volume of the urine in such balancing.

Figure 2:
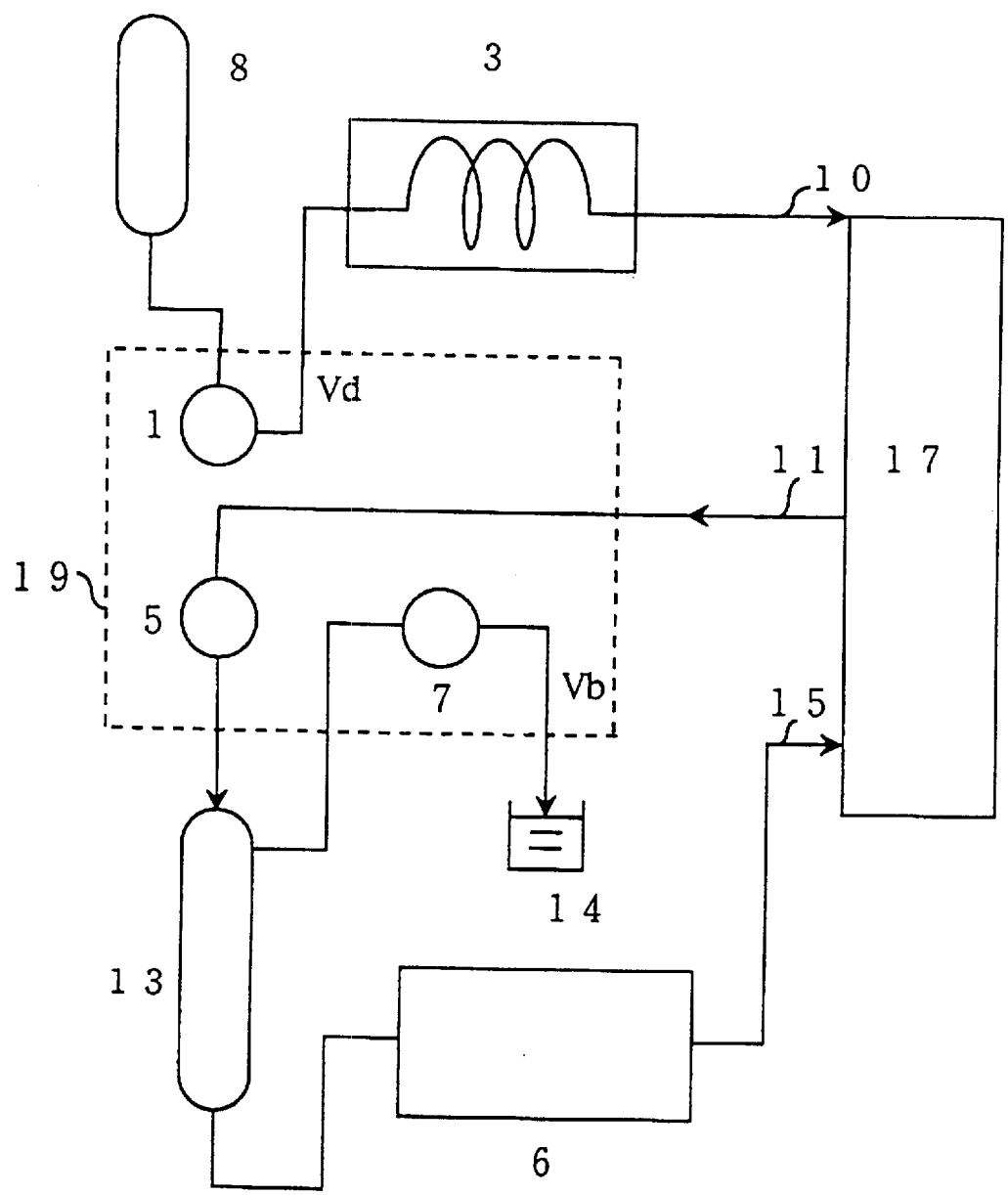
FIG. 2 shows a schematic view of an apparatus according to the present invention which comprises an injection/dehydration controlling mechanism.

FIG. 2 is a flow sheet schematically illustrating an apparatus according to the present invention which comprises an injection/dehydration controlling mechanism (19). An injection/dehydration controller preferably employed in the apparatus according to the present invention has not been employed in the field of the selective cooling method which is targeted by the apparatus according to the present invention. When using the injection/dehydration controller (19) in the apparatus according to the present invention, the flow rate of the diluent injected into the body, the flow rate of the blood drawn out from the body and the filtrate flow rate (thus, volumes pumped by the pumps (1), (5) and (7)) should be controlled, based on the object of the treatment, using the apparatus according to the present invention. Thus, the pumps (1) and (5), as well as the pump (7), if any, should be controlled as being organized with each other so that Vb and Vd are within the respective range of Vb and Vd described above and keep the relationship between Vb and Vd described above as well as the relationship between the total volume of the filtrate and the total volume of the diluent injected.

For example, it is not always necessary that a volume corresponding the volume of the diluent injected should be immediately filtered and separated as a filtrate. The diluent is rather preferred to be retained in a body for a certain time period, for the purpose of a treatment employing the selective cooling method, and thereafter drawn out slowly to avoid a plethora. For these purposes, it is preferred to adjust Vb and Vd appropriately by means of the injection/dehydration controller.

Alternatively, a non-contact hematocrit meter described above is preferably employed to perform an online determination of the hematocrit values of the diluted blood drawn out and/or the concentrated blood, based on the pumping rates of the pumps (1), (5) and (7) adjusted by means of an injection/dehydration controlling mechanism (19) so that the hematocrit value of the diluted blood is not lower than, for example, 5% as described above and/or the hematocrit value of the concentrated blood is, for example, at least 40%.

The use of the apparatus according to the present invention enables the maintenance of a local temperature at a certain desirable low temperature without problems.

The apparatus according to the present invention can be employed in any case where the selective cooling method is applied to a surgical operation. By cooling a lesion in a brain, a chest, an abdomen extremities with the diluent, the activity of an organ is suppressed thereby inhibiting the advancement of damage and a hypotensive condition is established thereby promoting the safety of the operation and reducing an amount of heparin and an amount of transfused blood, thus enabling a surgery without risk of infection.

In addition to surgery, the apparatus according to the present invention may be used for the maintenance of condition in a patient, especially the maintenance of a low activity condition. Thus, the use of the apparatus serves to keep a lesion surrounded by the diluted blood at a low temperature, thereby retarding or inhibiting the advancement of the disease.

For example, when it is desirable to cool a part of a body to a certain temperature, for example, a temperature within the range of about 30 to 15° C., preferably in a rapid procedure, but the temperature of another part must not be so lowered, for example, must not be lowered to a temperature as low as 28° C. or lower, then such part of the body can be exclusively cooled rapidly by means of the apparatus according to the present invention. In a typical case, it is desirable to exclusively and rapidly cool a brain to retard the swelling of the brain before the treatment of a cerebral bruise, but other parts must not be cooled. Since a part of a body can exclusively cooled but other parts are not so cooled especially when using the apparatus of the present invention, the entire body can be kept at a relatively higher temperature while keeping only a part at an extremely low temperature by adjusting the temperature and the volume of a diluent supplied, thereby enabling, in the treatment of a brain contusion, for example, as a result of a traffic accident, the exclusive rapid cooling of the brain, which is very useful, for example, in a craniotomy. In addition, the apparatus of the present invention causes no adverse reaction since it cools only a part of a body and does not so cool the other parts thereby enabling the part to be maintained. the low temperature for a prolonged period.

When the diluent is injected using the apparatus according to the present invention, the blood is diluted simultaneously with the cooling of a part of a body. Since the metabolic function of the cooled part is reduced (thus the oxygen consumption of the cooled tissue is reduced, and accordingly a low activity condition is maintained) as a result of the cooling, only such diluted blood is sufficient to be supplied to such cooled tissue. Therefore, in a surgery of such a lesion in which only such diluted blood is supplied, hemorrhaging can be reduced substantially.

The present invention provides an apparatus used to maintain the condition as described above, i.e., a condition maintaining apparatus. The term "condition maintenance" referred herein means maintenance in which a local or systemic low activity in a patient is established at a low temperature in order to retard or avoid the advancement of a disease.

As already mentioned at the beginning, the apparatus according to the present invention may be used in the treatment in animals including humans. The requirements including the parameters and the preferred embodiments disclosed herein can be generally employed in such a treatment, and more preferred embodiments can be selected when repetitive trials are performed in a concrete case.

For this purpose, the parameters for controlling the apparatus according to the present invention including vital data of a patient (a body weight, a hematocrit value, a part to be treated and the like), cooling data collected beforehand (a kind and a temperature of a diluent, a flow rate of the diluent supplied, a part to be cooled and its temperature change dependent on time, a flow rate of a diluted blood drawn out, temperature changes of the other parts and the like), a kind of treatment (a part to be treated, a treatment method, a treatment period and the like), and data of a filtration device (a kind of a filter material, a filtration pressure, a filtration rate and the like) are taken into consideration.

When these data are collected in various experiments and subjected to numerical analyses (regression), they will contribute to practical treatments.

Comparative Example

A catheter was inserted into a right vertebral artery in a cervical part of a beagle under a systemic anesthesia, and a lactated Ringer's solution cooled at 5° C. was injected as a cooled diluent at a rate of 70 ml/minute.

When a temperature of the brain determined in a left parietal region was lowered to 28° C. (5 minutes after initiation of the injection), the injection of the lactated Ringer's solution was terminated since the circulating blood volume reached a critical level.

EXAMPLES

Example 1

Using the apparatus shown in FIG. 1, a diluent was injected in experimental conditions similar to those in the Comparative Example described above, and after 3 minutes of the diluent supply, a diluted blood was drawn out via a jugular vein at 80 ml/min, and filtered using a commercial dialyzer (Model FB-10, Nipro) to obtain a concentrated blood, which was then heated in a thermostated tank to 38° C. and then returned into a right femoral vein via a catheter. In this case, the filtrate flow rate from the dialyzer was 40 ml/min (the filtrate began to be drained 3 minutes after the initiation of the injection).

20 Minutes after the initiation of the injection, the brain became to be capable of being kept at 20° C. or lower. Subsequently, the flow rate of the diluent injected was reduced to 30 ml/min and the body temperature could further be kept at 20° C. for about 40 minutes. Subsequently, the injection was terminated, and only the concentration operation was continued for 17 minutes.

The total volume of the cooling fluid injected was 3400 ml, and the total volume of the filtrate as a result of the dialysis was 2960 ml (at 40 ml/min for 74 minutes). In this case, the blood concentration was performed so that the hematocrit value recovered to about 40%.

No change in serum biochemical parameters was observed after the cooling, and TTC (triphenyltetrazolin chloride) staining revealed no ischemic lesions.

The beagle exhibited no neurological abnormality after the experiment.

Example 2

A catheter was inserted into a carotid artery in a human under a systemic anesthesia, and a lactated Ringer's solution cooled at 15° C. was injected at a flow rate of 105 ml/minute.

A temperature of the brain determined in a left cephalo-cervical region was lowered to 28° C. about 10 minutes after the initiation of the injection. Five minutes after the initiation of the diluent supply, diluted blood was drawn out via a jugular vein at 250 ml/min, and filtered using a commercial hemofilter (Model HF-2.1U, TORAY). A flow rate of filtrate was 100 ml/min. The filtered blood was heated in a thermostated tank to 38° C. and then returned into a femoral vein via a catheter.

What is claimed is:

1. An extracorporeal circulation apparatus for selectively cooling a body part of a mammal, said apparatus comprising:

a diluent supply unit for cooling a diluent and metering the cooled diluent into a blood vessel of a body part of a mammal such that blood of the body part of the mammal becomes diluted and the body part of the mammal becomes cooled, wherein said diluent supply unit includes (i) a fluid supply pump to discharge the diluent into the blood vessel of the mammal, (ii) a heat exchanger to cool the diluent before the diluent is discharged into the blood vessel of the mammal, (iii) a container to supply the diluent to said fluid supply pump, (iv) a catheter to supply the diluent, after the diluent has been discharged from said fluid supply pump and after the diluent has been cooled by said heat exchanger, into the blood vessel of the body part of the mammal, (v) a flow meter to determine the flow rate of the diluent discharged from said fluid supply pump, (vi) a thermometer to determine the temperature of the diluent after the diluent has been cooled by said heat exchanger and before the diluent is supplied into the blood vessel of the body part of the mammal, and (vii) a drip chamber to remove air bubbles from the diluent before the diluent is supplied into the blood vessel of the body part of the mammal;

a blood concentration unit for metering the diluted blood from a blood vessel of the mammal and for concentrating the metered diluted blood to form concentrated blood; and a blood supply unit for heating the concentrated blood and metering the heated concentrated blood into a blood vessel of the mammal.

2. The extracorporeal circulation apparatus according to claim 1, wherein said blood concentration unit includes a drawing-out/fluid supply pump to meter the diluted blood from a blood vessel of the mammal, and a blood concentration device to concentrate the diluted blood.

3. The extracorporeal circulation apparatus according to claim 2, wherein said blood supply unit includes a heat exchanger to heat the concentrated blood prior to metering the concentrated blood into a blood vessel of the mammal.

4. The extracorporeal circulation apparatus according to claim 3, and further comprising a control device to control said fluid supply pump and said drawing-out/fluid supply pump such that the flow rate of the diluent supplied into the blood vessel of the mammal and the flow rate of blood metered from the mammal can be controlled.

5. The extracorporeal circulation apparatus according to claim 2, wherein said blood concentration unit further includes a filtrate pump connected to said blood concentration device to adjust the pressure within said blood concentration device, and further comprising a control device to control said fluid supply pump, said drawing-out/fluid supply pump and said filtrate pump such that the flow rate of the diluent supplied into the blood vessel of the mammal, the flow rate of blood metered from the mammal and a filtrate flow rate can be controlled.

6. The extracorporeal circulation apparatus according to claim 1, wherein said blood supply unit includes a heat exchanger to heat the concentrated blood prior to metering the concentrated blood into a blood vessel of the mammal.

7. The extracorporeal circulation apparatus according to claim 6, wherein said blood supply unit further includes a catheter to meter the heated concentrated blood into a blood vessel of the mammal.

8. The extracorporeal circulation apparatus according to claim 7, wherein said blood supply unit further includes a drip chamber to remove air bubbles from the concentrated blood before the heated concentrated blood is metered into a blood vessel of the mammal.

9. The extracorporeal circulation apparatus according to claim 1, wherein said diluent supply unit is operable to cool the diluent to a temperature within the range of from 25° C. to 3° C.

10. The extracorporeal circulation apparatus according to claim 1, wherein said diluent supply unit is operable to maintain a flow rate of the cooled diluent being metered into the blood vessel of the body part of the mammal within the range of from 100 ml/min to 600 ml/min.

11. The extracorporeal circulation apparatus according to claim 1, wherein said blood concentration unit includes a filtration element having a filtrate flow rate within the range of from 30 ml/min to 200 ml/min.

12. The extracorporeal circulation apparatus according to claim 1, wherein said blood concentration unit is operable to concentrate the diluted blood to achieve a hematocrit value that is at least 80% of a hematocrit value of the blood before dilution of the blood.

13. The extracorporeal circulation apparatus according to claim 1, and further comprising an injection/dehydration controlling mechanism.

14. The extracorporeal circulation apparatus according to claim 1, wherein said blood supply unit includes a heat exchanger.

15. The extracorporeal circulation apparatus according to claim 1, wherein said heat exchanger is operable to cool the diluent to a temperature within the range of from 25° C. to 3° C.

16. The extracorporeal circulation apparatus according to claim 1, wherein said fluid supply pump is operable to maintain a flow rate of the cooled diluent being metered into the blood vessel of the mammal within the range of from 100 ml/min to 600 ml/min.

17. An extracorporeal circulation apparatus for selectively cooling a body part of a mammal, said apparatus comprising:

a diluent supply unit for cooling a diluent and metering the cooled diluent into a blood vessel of a body part of a mammal such that blood of the body part of the mammal becomes diluted and the body part of the mammal becomes cooled;

a blood concentration unit for metering the diluted blood from a blood vessel of the mammal and for concentrating the metered diluted blood to form concentrated blood, wherein said blood concentration unit includes (i) a drawing-out/fluid supply pump for metering the diluted blood from the mammal, (ii) a blood concentration device to concentrate the diluted blood, (iii) a catheter to supply the metered diluted blood from a blood vessel of the mammal to said drawing-out/fluid supply pump, (iv) an anticoagulant supply unit to supply an anticoagulant to the diluted blood after the diluted blood has been metered from a blood vessel of the mammal, and (v) a drip chamber to remove air bubbles from the diluted blood after the diluted blood has been metered from a blood vessel of the mammal but before the diluted blood is supplied to said blood concentration device; and a blood supply unit for heating the concentrated blood and metering the heated concentrated blood into a blood vessel of the mammal.

18. The extracorporeal circulation apparatus according to claim 17, wherein said blood concentration unit includes a drawing-out/fluid supply pump to meter the diluted blood from a blood vessel of the mammal, and a blood concentration device to concentrate the diluted blood.

19. The extracorporeal circulation apparatus according to claim 18, wherein said blood supply unit includes a heat exchanger to heat the concentrated blood prior to metering the concentrated blood into a blood vessel of the mammal.

20. The extracorporeal circulation apparatus according to claim 19, and further comprising a control device to control said fluid supply pump and said drawing-out/fluid supply pump such that the flow rate of the diluent supplied into the blood vessel of the mammal and the flow rate of blood metered from the mammal can be controlled.

21. The extracorporeal circulation apparatus according to claim 18, wherein said blood concentration unit further includes a filtrate pump connected to said blood concentration device to adjust the pressure within said blood concentration device, and further comprising a control device to control said fluid supply pump, said drawing-out/fluid supply pump and said filtrate pump such that the flow rate of the diluent supplied into the blood vessel of the mammal, the flow rate of blood metered from the mammal and a filtrate flow rate can be controlled.

22. The extracorporeal circulation apparatus according to claim 17, wherein said blood supply unit includes a heat exchanger to heat the concentrated blood prior to metering the concentrated blood into a blood vessel of the mammal.

23. The extracorporeal circulation apparatus according to claim 22, wherein said blood supply unit further includes a catheter to meter the heated concentrated blood into a blood vessel of the mammal.

24. The extracorporeal circulation apparatus according to claim 23, wherein said blood supply unit further includes a drip chamber to remove air bubbles from the concentrated blood before the heated concentrated blood is metered into a blood vessel of the mammal.

25. The extracorporeal circulation apparatus according to claim 17, wherein said diluent supply unit is operable to cool the diluent to a temperature within the range of from 25° C. to 3° C.

26. The extracorporeal circulation apparatus according to claim 17, wherein said diluent supply unit is operable to maintain a flow rate of the cooled diluent being metered into the blood vessel of the body part of the mammal within the range of from 100 ml/min to 600 ml/min.

27. The extracorporeal circulation apparatus according to claim 17, wherein said blood concentration unit includes a filtration element having a filtrate flow rate within the range of from 30 ml/min to 200 ml/min.

28. The extracorporeal circulation apparatus according to claim 17, wherein said blood concentration unit is operable to concentrate the diluted blood to achieve a hematocrit value that is at least 80% of a hematocrit value of the blood before dilution of the blood.

29. The extracorporeal circulation apparatus according to claim 17, and further comprising an injection/dehydration controlling mechanism.

30. The extracorporeal circulation apparatus according to claim 17, wherein said blood supply unit includes a heat exchanger.

31. The extracorporeal circulation apparatus according to claim 17, wherein said blood concentration unit further includes a filtrate pump connected to said blood concentration device to adjust the pressure within said blood concentration device.

* * * * *